United States Patent [19]
Ota et al.

[11] Patent Number: 5,778,879
[45] Date of Patent: Jul. 14, 1998

[54] ELECTRONIC BLOOD PRESSURE METER WITH POSTURE DETECTOR

[75] Inventors: Hiroyuki Ota, Moriyama; Kenji Taniguchi, Kyoto, both of Japan

[73] Assignee: Omron Corporation, Kyoto, Japan

[21] Appl. No.: 606,279

[22] Filed: Feb. 23, 1996

[30] Foreign Application Priority Data

Feb. 16, 1995 [JP] Japan ..................................... 7-28065

[51] Int. Cl.[6] ............................................... A61B 5/02
[52] U.S. Cl. ........................... 128/672; 128/680; 128/690
[58] Field of Search .................................. 128/670–672, 128/677, 680–684, 686, 690, 691

[56] References Cited

U.S. PATENT DOCUMENTS

| 4,998,534 | 3/1991 | Claxton, III et al. ............ 128/681 X |
| 5,201,319 | 4/1993 | Negishi ............................. 128/672 |

*Primary Examiner*—Jennifer Bahr
*Assistant Examiner*—Ryan Carter
*Attorney, Agent, or Firm*—Morrison & Foerster LLP

[57] ABSTRACT

This invention provides an electronic blood pressure meter which can measure blood pressure with great accuracy. The angle of inclination is detected by inclination sensor and the height of the limb where the measurement is to be taken is obtained from this angle of inclination. An MPU determines whether the height which is obtained is within a specified difference from the height of the heart. The result of this determination is communicated via display or buzzer.

6 Claims, 6 Drawing Sheets

5,778,879

1

ELECTRONIC BLOOD PRESSURE METER WITH POSTURE DETECTOR

FIELD OF THE INVENTION

This invention concerns an blood pressure meter with a posture detector for indicating when the blood pressure meter is not positioned level with a patient's heart so as to ensure that an accurate measurement can be made.

BACKGROUND OF THE INVENTION

In general, blood pressure meters have a cuff which is fastened to a patient's wrist or finger, body parts which can move freely. However, for accurate measurements, the cuff must be positioned at a height level with the patient's heart. If the cuff is not positioned level with the heart, a measurement error will result.

To prevent such errors, commonly assigned Japanese patent application, Laid-Open Patent Application No. 63-311929, discloses a device, such as that illustrated in FIG. 9, requiring that the positional relationship (i.e., the height difference) between the wrist or finger cuff 71 and the heart be manually determined and input by setting knob 70 to a corresponding height. In the illustrated example, if the height of the cuff 71 is 10 cm lower than the patient's heart, the height adjustment knob 70 is set at the "−1" position to offset the blood pressure by −8 mm Hg to ensure that an accurate measurement can be made. Similarly, if the height of the cuff 71 is 10 cm higher than the patient's heart, the knob 70 is set at the "+1" position to offset the blood pressure by +8 mm Hg. A value corresponding to this difference is then used to perform a calculation on the blood pressure value obtained by the measurement device to obtain a corrected value.

With existing electronic blood pressure meters of the type described above, accurate assessment of the positional relationship between the wrist or finger cuff and the heart is difficult, and a value for this relationship is required to be input each time a blood pressure measurement is taken. Thus, using these devices is tedious, and mistakes in entering the value results in measurement errors, making this type of blood pressure meter prone to be affected by human error.

SUMMARY OF THE INVENTION

Accordingly, the present invention provides an electronic blood pressure meter with a posture detector which detects attempts to take a measurement of an improperly positioned patient, and which indicates this state to enable appropriate repositioning of the patient.

The electronic blood pressure meter of this invention comprises a blood pressure meter which is configured with a cuff device which, when fastened to a given part of the body, extracts data concerning the pulsewave found in that body part, and a device which measures either the blood pressure or the condition of the blood vessels based on the extracted pulsewave data. This blood pressure meter is equipped with a posture detector which detects the posture of the patient and a judging device which judges whether the detected posture is appropriate for measuring blood pressure. If this judging device determines that the posture is not the appropriate one, this fact is communicated, to permit repositioning of the patient to a correct posture.

2

Figure 3:
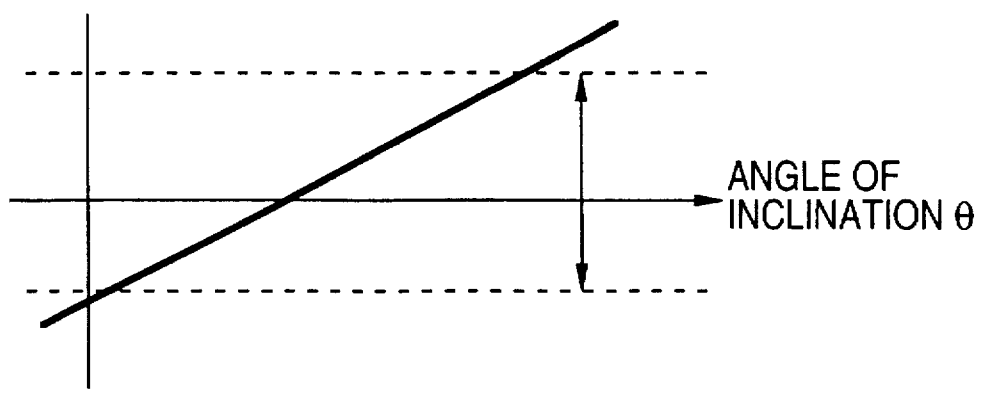

FIG. 3 shows the relationship between the angle of inclination of the limb and the height difference.

Figure 4:
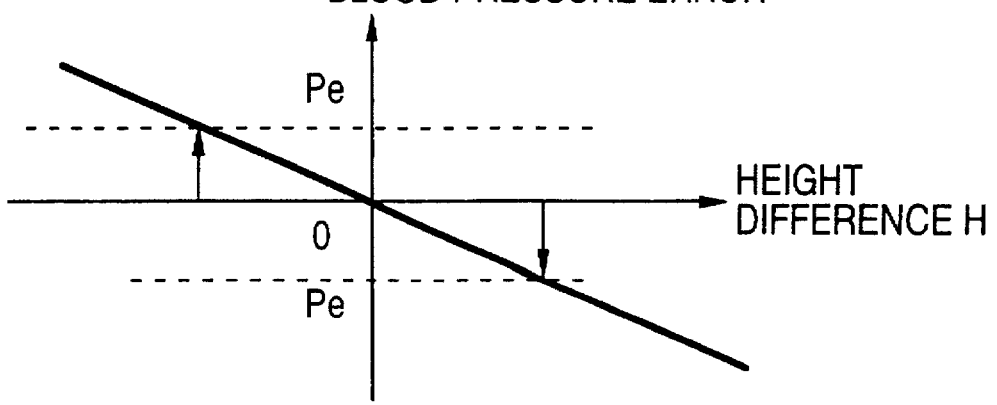

FIG. 4 shows the relationship between the height difference and the measurement error.

Figure 5:
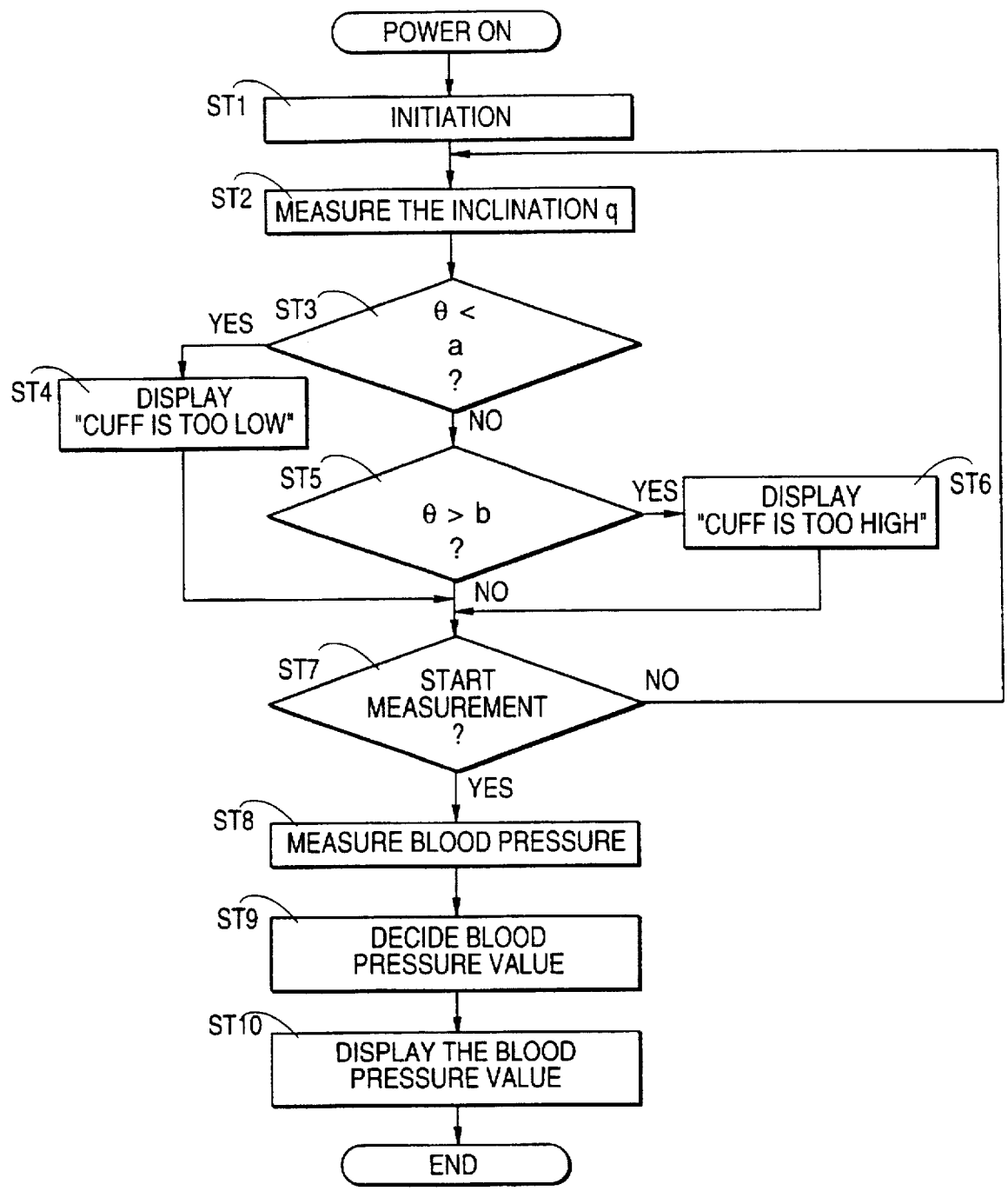

FIG. 5 is a flowchart of the operations performed by a wrist-type electronic blood pressure meter according to the first embodiment of the present invention.

Figure 6:
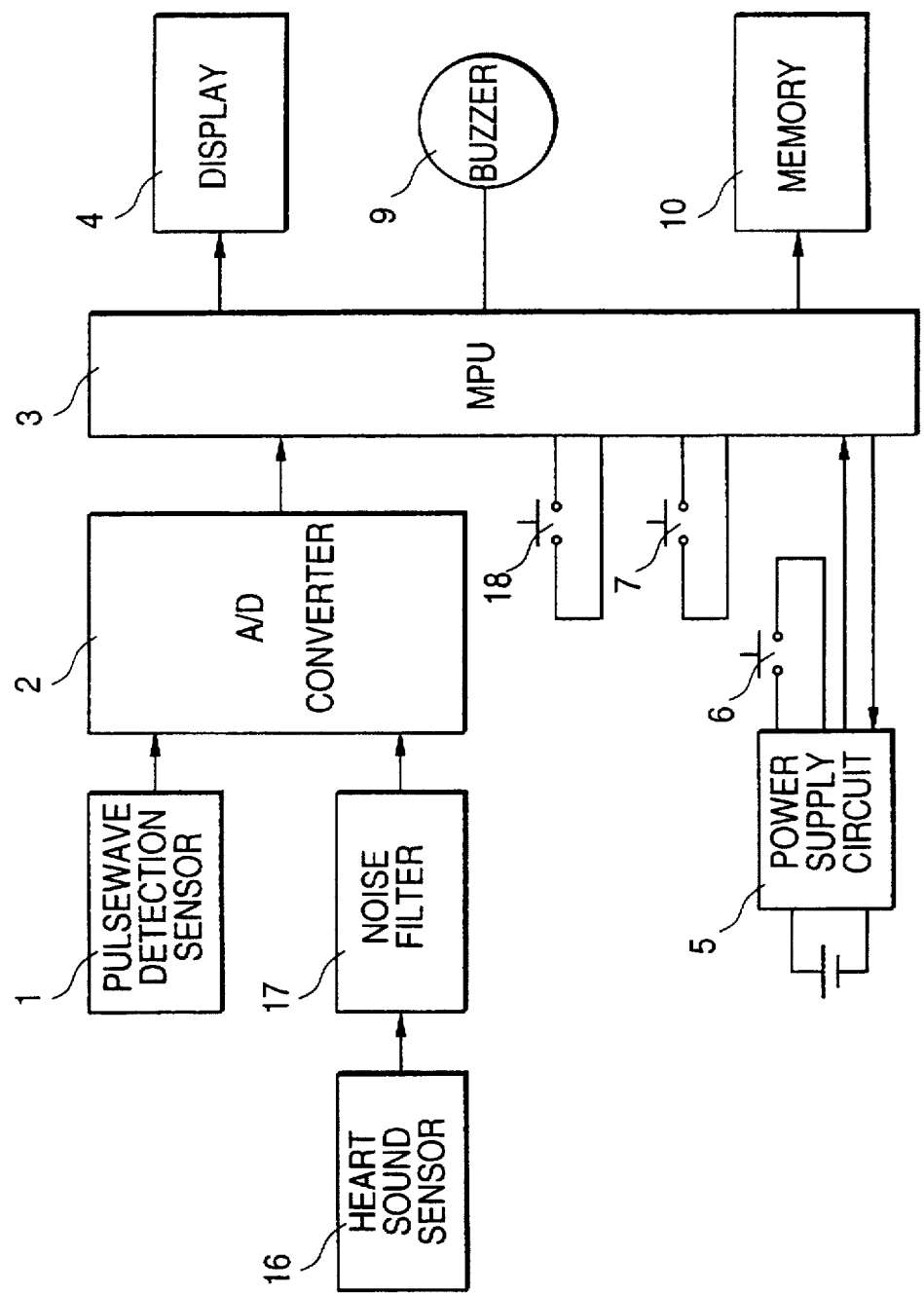

FIG. 6 is a block diagram of a second embodiment of the present invention, illustrating a wrist-type electronic blood pressure meter.

Figure 7:
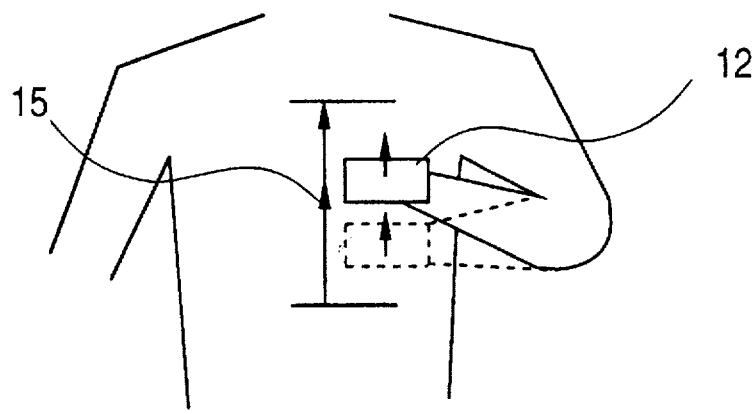

FIG. 7 illustrates alignment between the limb on which the measurement is to be made and the heart.

Figure 8:
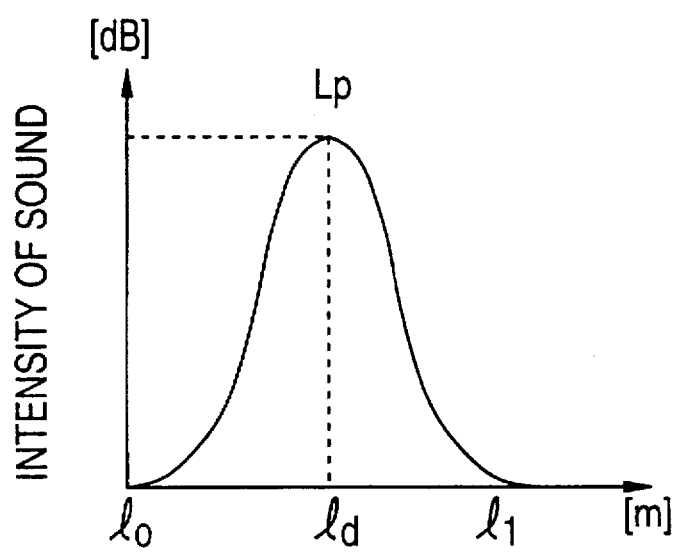

FIG. 8 illustrates the relationship between the height of the limb and the intensity of the heart sounds.

Figure 9:
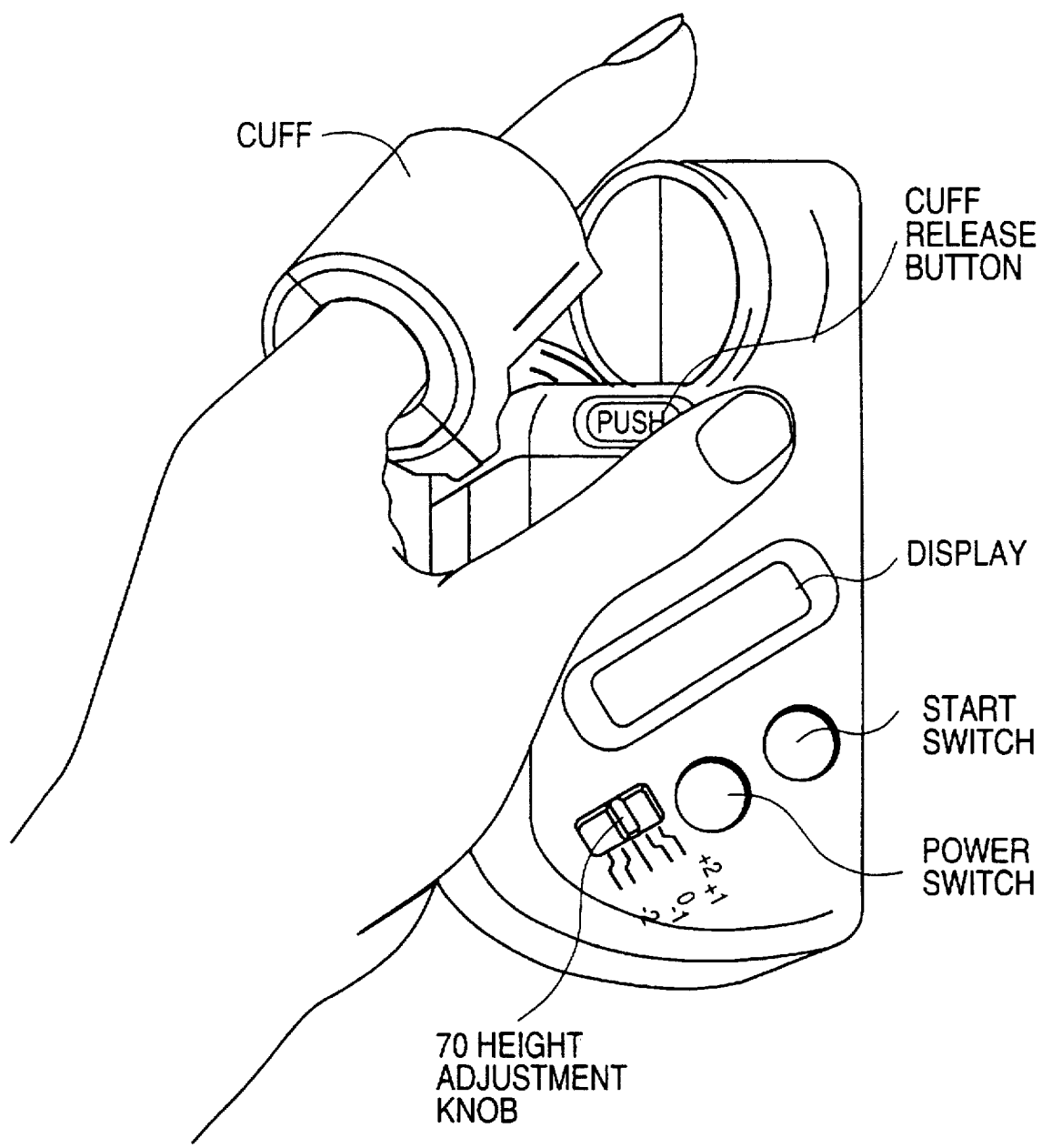

FIG. 9 illustrates a prior art finger type blood pressure meter with a manual height adjustment.

DETAILED DESCRIPTION OF THE INVENTION

We shall now give a more detailed explanation of the present invention, with reference to a first embodiment.

Figure 1:
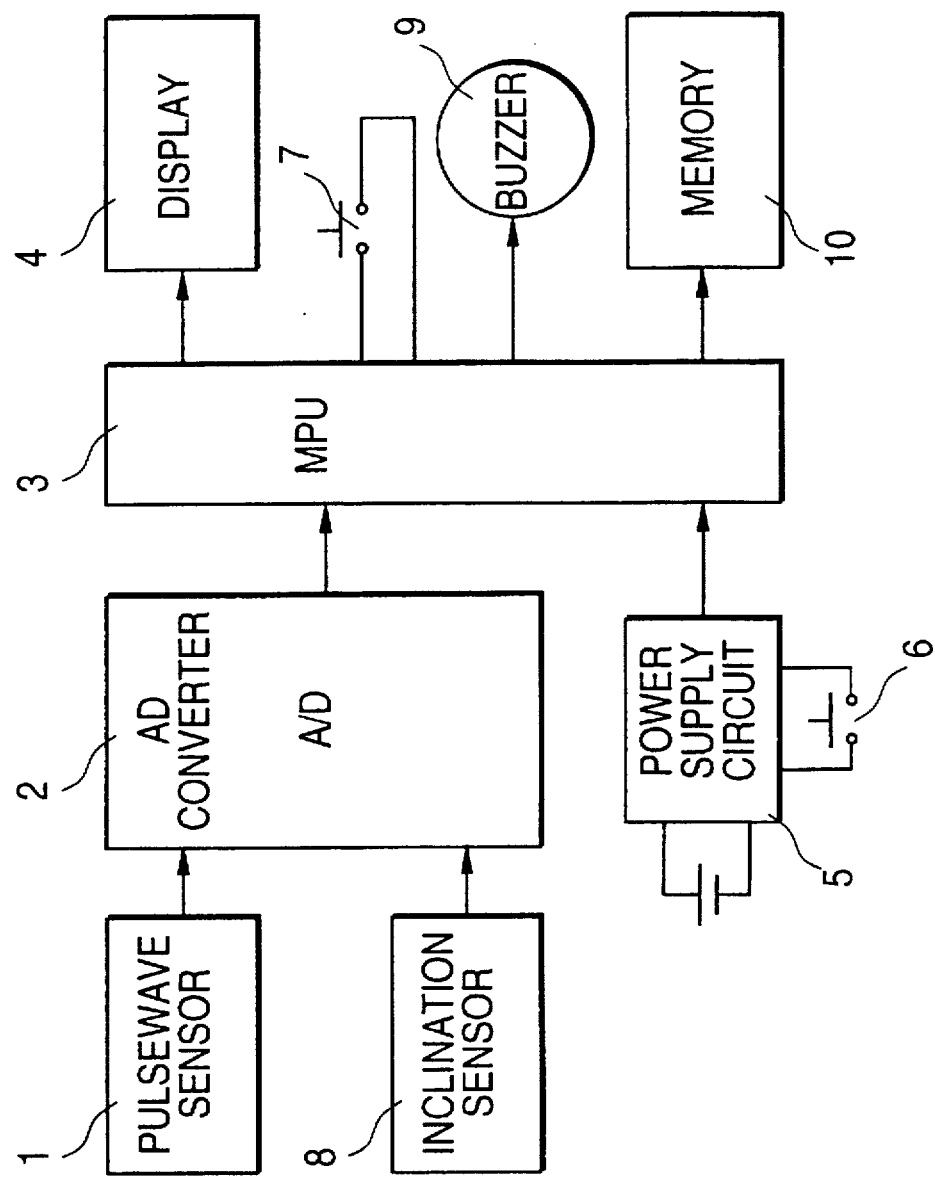
FIG. 1 is a block diagram of a first embodiment of the present invention, illustrating a wrist-type electronic blood pressure meter.

FIG. 1 is a block diagram of a wrist-type electronic blood pressure meter, according to the first embodiment of the present invention. This electronic blood pressure meter comprises: pulsewave sensor 1, which detects a pulsewave; A/D converter 2, which converts the detected pulsewave to a digital signal; MPU (microprocessor unit) 3, which executes the processing required to measure the blood pressure; display 4, which displays the measured blood pressure value, the number of pulses, and other relevant data; power supply circuit 5, which supplies power supply voltage to the other various circuits; power supply switch 6; start switch 7; inclination sensor 8, which detects the height of the cuff; buzzer 9, which indicates incorrect posture; and memory 10. Although not shown in the drawing, display 4 is an intrinsic part of the device, and the cuff is an integral part of the blood pressure meter.

Display 4 might, for example, be an LCD panel to display numerical or character values for the blood pressure and the pulse rate. If the device were being held at an incorrect level, it could be configured to display, for example, symbols to communicate this fact and give appropriate instructions.

Figure 2:
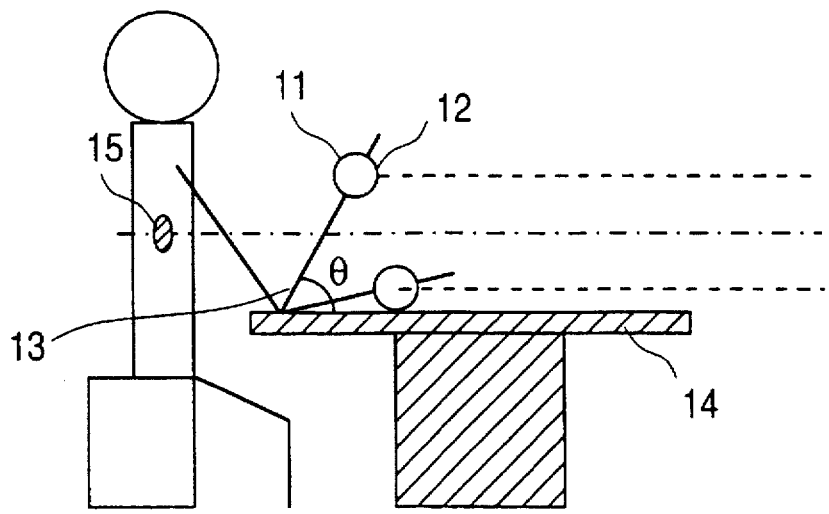
FIG. 2 illustrates the relationship between the angle of inclination of the limb on which the measurement is to be taken, and the height of the limb and the height of the heart.

We shall next explain the relationship between inclination and height. In this example shown in FIG. 2, blood pressure meter 12 is fastened to the patient's wrist 11. The patient's arm 13, rests on table 14, and the angle between arm 13 and the surface of table 14 is labelled Θ. The height difference between the patient's heart 15 and blood pressure meter 12 (at the part of the body on which the measurement is to be taken) is referred to herein as height difference H.

FIG. 3 illustrates a possible relationship between angle of inclination Θ and height difference H. Thus, height difference H may be derived from angle of inclination Θ. Accordingly, by using an inclination sensor to determine angle of inclination Θ, the height of the blood pressure meter 12 can be determined.

FIG. 4 illustrates the relationship between the height difference H and the measurement error. When the measurement error exceeds a predetermined threshold $\pm P_c$, the height difference H is determined to be too large, and the height, or position, of the body part where the measurement is to be taken is incorrect. This state may be communicated via display 4 and/or buzzer 9, to enable correct repositioning of the patient's body part.

We shall next discuss the measurement operation executed by this embodiment with reference to the flowchart of FIG. 5. When power supply switch 6 is turned on, processing is executed to initialize the circuits in step 1

(indicated in FIG. 5 as ST 1). Inclination sensor 8 detects the current angle of inclination Θ of blood pressure meter 12. This angle is transmitted to MPU 3 by way of A/D converter 2 and stored in memory 10 as angle of inclination Θ (ST 2). It is then determined whether angle Θ is smaller than a given value a (ST 3). If it is, the answer in Step 3 will be "yes." Message "Cuff is too low" will appear on display 4 (ST 4), and buzzer 9 may be sounded. If angle Θ is found to be greater than or equal to value a in Step 3, it is determined whether angle Θ is greater than a given value b, where b is greater than a (ST 5). If it is, the answer will be "yes," "Cuff is too high" will appear on display 4 (Step 6), and buzzer 9 may be sounded. If angle Θ is such that a≦Θ≦b, display 4 will not indicate that the cuff is too high and buzzer 9 will not sound. When start switch 7 is turned on (ST 7), measurement begins (ST 8).

The blood pressure may be measured using any appropriate method. For example, the wrist may be pressurized by the cuff and the pressure increased until a given pressure is achieved in the cuff. The pressure is then decreased. The data series representing the amplitude of the pulsewaves detected by pulsewave sensor 1 during pressurization and depressurization and the cuff pressure are used to determine the maximum (i.e., systolic) pressure, which is then shown on display 4 (ST 9). The minimum (i.e., diastolic) pressure is then determined and displayed in the same fashion (ST 10).

FIG. 6 is a block diagram of a wrist-type electronic blood pressure meter, according to a second embodiment of the present invention. This blood pressure meter comprises: pulsewave sensor 1, which detects a pulsewave; A/D converter 2, which converts the detected pulsewave to a digital signal; MPU (microprocessor unit) 3, which executes the processing required to measure the blood pressure; display 4, which displays the measured blood pressure value, the pulse rate, and other relevant data; power supply circuit 5, which supplies power supply voltage to the other various circuits; power supply switch 6; start switch 7; buzzer 9, which indicates when the patient's posture is incorrect; memory 10; heart sound sensor 16, which detects the height of the part of the body on which the measurement is to be taken; noise filter 17, which removes the noise component from the signal detected by heart sound sensor 16; and memory switch 18.

In this embodiment, blood pressure meter 12 is fastened to the wrist, and must be held at the level of the patient's heart 15, as shown in FIG. 7. To find this level, heart sound sensor 16 is used to search in the vicinity of the patient's heart for the location where the heart sounds are most intense. This location where the intensity peaks is indicated in FIG. 8 as point $L_P$, and indicates the location of the patient's heart. The detection of point $L_P$ may be communicated via display 4 or by sounding buzzer 9.

To test the reproducibility of the measurement, memory switch 18 may be turned on to record in memory 10 the value of point $L_P$, the peak intensity of the heart sounds, found before taking the first measurement. Subsequent measurements can then be taken in the location where this value is found.

When blood pressure meter 12 is correctly positioned, i.e., when it is aligned with the heart, start switch 7 is turned on and the processing required to measure the blood pressure commences.

With this embodiment, the intensity of the heart sounds is detected in the part of the body where the measurement is to be taken. The location is detected where the intensity of the heart sounds peaks, and is communicated to enable positioning of the patient's wrist (in this case), level with the patient's heart. This ensures that the blood pressure can be measured accurately. Quantifying, displaying and storing the intensity of the heart sounds makes it easier to align the wrist with the heart each time a measurement is to be taken, and it enhances the reproducibility of the measurement. Since only a single location, that where the heart sounds are most intense, need be detected, a circuit of a simple configuration can be used. With the design described above, the circuit board can be enclosed within a single case.

In the embodiments described above, a pulsewave sensor is used in a wrist-type electronic blood pressure meter to extract pulsewave data. However, variations are possible. For example, this invention may be implemented in an electronic blood pressure meter which extracts the pulsewave component contained in the cuff pressure. In another variation, this invention may be applied in a blood pressure meter which is freely movable from limb to limb, such as a finger-type meter.

Although the present invention has been described in terms of specific embodiments, the invention is not limited to these specific embodiments. Rather, the scope of the invention is defined by the following claims, and other embodiments are within the scope of the claims.

What is claimed is:

1. An electronic blood pressure meter, comprising:
   a cuff device which, when fastened to a given part of a body, extracts data concerning pulsewave information found in said given body part;
   a device which measures either a blood pressure or condition of blood vessels based on said extracted pulsewave information;
   a posture detecting device which detects the posture of said given body part by detecting the height of said body part on which a blood pressure measurement is being performed; and
   a judging device which judges whether said detected posture is appropriate.

2. The electronic blood pressure meter according to claim 1, wherein said posture detecting device detects the inclination of said given body part.

3. The electronic blood pressure monitor according to claim 1, wherein said cuff device is movable relative to said device which measures either a blood pressure or condition of blood vessels.

4. An electronic blood pressure meter, comprising:
   a cuff device which, when fastened to a given part of a body, extracts data concerning pulsewave information found in said given body part;
   a device which measures either a blood pressure or condition of blood vessels based on said extracted pulsewave information;
   a posture detecting device comprising a heart sound sensor which detects the posture of said given body part; and
   a judging device which judges whether said detected posture is appropriate.

5. The electronic blood pressure meter according to claim 4, further comprising:
   a height difference detector for detecting the height difference between the height of a heart of the body and the height of the body part at the detected posture,
   wherein the judging device judges whether the detected posture is appropriate based on the detected height difference.

6. The electronic blood pressure monitor according to claim 4, wherein said cuff device is movable relative to said device which measures either a blood pressure or condition of blood vessels.

* * * * *